(12) United States Patent
Yu et al.

(10) Patent No.: US 7,361,486 B2
(45) Date of Patent: Apr. 22, 2008

(54) POLYNUCLEOTIDE, VECTOR, HOST CELL AND METHOD FOR PRODUCING HUMAN HEPATOMA-DERIVED GROWTH FACTOR 5 POLYPEPTIDE

(75) Inventors: Long Yu, 220 Handan Road, Shanghai (CN) 200433; Lisha Tang, Shanghai (CN); Zekun Guo, Shanghai (CN); Pingzhao Zhang, Shanghai (CN); Yimin Dong, Shanghai (CN)

(73) Assignee: Long Yu, Shanghai (CN)

( * ) Notice: Subject to any disclaimer, the term of this patent is extended or adjusted under 35 U.S.C. 154(b) by 289 days.

(21) Appl. No.: 10/501,053

(22) PCT Filed: Jan. 2, 2003

(86) PCT No.: PCT/CN03/00003

§ 371 (c)(1),
(2), (4) Date: Jul. 9, 2004

(87) PCT Pub. No.: WO03/057883

PCT Pub. Date: Jul. 17, 2003

(65) Prior Publication Data

US 2005/0080241 A1 Apr. 14, 2005

(30) Foreign Application Priority Data

Jan. 11, 2002 (CN) .................. 2002 1 0010535

(51) Int. Cl.
| C12N 15/18 | (2006.01) |
| C12N 15/63 | (2006.01) |
| C07H 21/04 | (2006.01) |
| C07K 14/475 | (2006.01) |
| C12N 1/21 | (2006.01) |
| C12N 5/10 | (2006.01) |

(52) U.S. Cl. .............. 435/69.1; 435/69.4; 435/320.1; 435/243; 435/325; 530/399

(58) Field of Classification Search .............. None
See application file for complete search history.

(56) References Cited

U.S. PATENT DOCUMENTS 5,235,042 A  8/1993  Klagsbrun

FOREIGN PATENT DOCUMENTS

| WO | WO 87/06239 | 10/1987 |
| WO | WO 94/01548 | * 1/1994 |
| WO | WO 96/39485 | 12/1996 |
| WO | WO 00/37492 | 6/2000 |

OTHER PUBLICATIONS

Tirado et al. (GenBank Acc. No. AY061636, Nov. 13, 2001), "A new member of the HDGF family, an apoptotic role?".*
Ikegame, K., et al., "A New Member of a Hepatoma-Derived Growth Factor Gene Family Can Translocate to the Nucleus", Biochemical and Biophysical Research Communications 266, 81-87 (1999).
Izumoto, Y., et al., "Hepatoma-Derived Growth Factor Belongs to a Gene Family in Mice Showing Significant Homology in the Amino Terminus", Biochemical and Biophysical Research Communications 238, 26-32 (1997).
Klagsbrun et al., "Human tumor cells synthesize an endothelial cell growth factor that is structurally related to basic fibroblast growth factor" Proc. Natl. Acad. Sci. USA vol. 83, pp. 2448-2452 Apr. 1986.

* cited by examiner

*Primary Examiner*—Christine J Saoud
(74) *Attorney, Agent, or Firm*—Hamre, Schumann, Mueller & Larson, P.C.

(57) ABSTRACT

The invention provides a cDNA sequence of human hepatoma derived growth factor 5 (HDGF5). The present invention also relates to the polypeptides encoded by the nucleotide sequences, the uses of these polynucleotides and polypeptides, and the methods for producing HDGF5 polynucleotides and polypeptides.

7 Claims, 1 Drawing Sheet

```
human HDGF5   MSCFSRPK-YKTGDLVFAKLKGYAHWPARIEHVTEP-------NRYQVFFFGTHETAFLGP 53
rat HRP       MSCFSRPK-YKTGDLVFAKLKGYAHWPARIEHVTEP-------NRYQVFFFGTHETALLGP 53
mouse HRP1    MSCFSRSK-YKTGDLVFAKLKGYAHWPARIEHVAEA-------NRYQVFFFGTHETALLGP 53
mouse HDGF    MSRSNRQKEYKCGDLVFAKMKGYPHWPARIDEMPEAAVKSTANKYQVFFFGTHETAFLGP 60
rat HDGF      MSRSNRQKEYKCGDLVFAKMKGYPHWPARIDEMPEAAVKSTANKYQVFFFGTHETAFLGP 60
human HDGF    MSRSNRQKEYKCGDLVFAKMKGYPHWPARIDEMPEAAVKSTANKYQVFFFGTHETAFLGP 60
human HRP1    MSRSNRQKEYKCGDLVFAKMKGYPHWPARIDEMPEAAVKSTANKYQVFFFGTHETAFLGP 60
human HRP3    -MARPRPREYKAGDLVFAKMKGYPHWPARIDELPEGAVKPPANKYPIFFFGTHETAFLGP 59
mouse HRP3    -MARPRPREYKAGDLVFAKMKGYPHWPARIDELPEGAVKPPANKYPIFFFGTHETAFLGP 59
mouse HRP2    ----MPHAFKPGDLVFAKMKGYPHWPARIDDIADGAVKPPPNKYPIFFFGTHETAFLGP 55
rat HDGF3     ----MPHAFKPGDLVFAKMKGYPHWPARIDDIADGAVKPPPNKYPIFFFGTHETAFLGP 55
                 :* *****:*.*****:.:.:    *:* :*******:* human HDGF5   KHLFPYEESKERFGKPNKRRGFSEGLWEIEHDPMAEASPCLCPDEEQLCAEEPGPGEEPE 113  (SEQ ID NO:2)
rat HRP       KHLFPYEESKERFGKPNKRRGFSEGLWEIEHDPMVEASPCLCPDEEQLCAEEPGPGEEPE 113  (SEQ ID NO:9)
mouse HRP1    RHLFPYEESKEKFGKPNKRRGFSEGLWEIEHDPMVEASSSLCSEEDQSYTEDPGLAEEPE 113  (SEQ ID NO:10)
mouse HDGF    KDLFPYEESKEKFGKPNKRKGFSEGLWEIENNPTVKASGYQSS-QKKSCAAEP------- 112  (SEQ ID NO:11)
rat HDGF      KDLFPYEESKEKFGKPNKRKGFSEGLWEIENNPTVKASGYQSS-QKKSCAAEP------- 112  (SEQ ID NO:12)
human HDGF    KDLFPYEESKEKFGKPNKRKGFSEGLWEIENNPTVKASGYQSS-QKKSCVEEP------- 112  (SEQ ID NO:13)
human HRP1    KDLFPYEESKEKFGKPNKRKGFSEGLWEIENNPTVKASGYQSS-QKKSCVEEP------- 112  (SEQ ID NO:14)
human HRP3    KDLFPYKEYKDKFGKSNKRKGFNEGLWEIENNPGVKFTGYQAIQQQSSSETEGEGGNTAD 119  (SEQ ID NO:15)
mouse HRP3    KDLFPYKEYKDKFGKSNKRKGFNEGLWEIENNPGVKFTGYQTIQQQSSSETEGEGGNTAD 119  (SEQ ID NO:16)
mouse HRP2    KDLFPYDKCKDKYGKPNKRKGFNEGLWEIQNNPHASYSAPPPVSSSDSEAPEADLGCGSD 116  (SEQ ID NO:17)
rat HDGF3     KDLFPYDKCKDKYGKPNKRKGFNEGLWEIQNNPHASYSAPLPVSSSDSEAPEADLGGGSD 115  (SEQ ID NO:18)
              :.****.: *:::**.**:**.*****:::* .. :     ... :
```

Fig. 1

SEQUENCE LISTING

<160> NUMBER OF SEQ ID NOS: 8

<210> SEQ ID NO 1
<211> LENGTH: 990
<212> TYPE: DNA

<213> ORGANISM: Homo sapiens
<220> FEATURE:
<221> NAME/KEY: CDS
<222> LOCATION: (5)..(910)
<223> OTHER INFORMATION:

<400> SEQUENCE: 1

```
cgct atg tct tgc ttc agc cgc cca aaa tac aag acc ggg gac ctg gtg        49
     Met Ser Cys Phe Ser Arg Pro Lys Tyr Lys Thr Gly Asp Leu Val
      1               5                  10                  15 ttt gcc aaa tta aag ggc tat gcc cat tgg cca gcg agg att gaa cat         97
Phe Ala Lys Leu Lys Gly Tyr Ala His Trp Pro Ala Arg Ile Glu His
             20                  25                  30 gtc act gaa ccc aac cgc tac cag gtg ttc ttc ttt ggg acc cat gag        145
Val Thr Glu Pro Asn Arg Tyr Gln Val Phe Phe Phe Gly Thr His Glu
         35                  40                  45 acc gcc ctg ctg ggc ccc aag cac ctt ttt cct tat gag gag tcc aag        193
Thr Ala Leu Leu Gly Pro Lys His Leu Phe Pro Tyr Glu Glu Ser Lys
     50                  55                  60 gag agg ttc ggc aag cct aac aag agg cgc ggc ttc agt gag ggg ctg        241
Glu Arg Phe Gly Lys Pro Asn Lys Arg Arg Gly Phe Ser Glu Gly Leu
 65                  70                  75 tgg gag atc gag cac gac cct atg gct gag gcc tcc cct tgc ctg tgc        289
Trp Glu Ile Glu His Asp Pro Met Ala Glu Ala Ser Pro Cys Leu Cys
 80                  85                  90                  95 cca gat gag gag cag ctt tgt gcc gag gag cca ggg cca gga gag gag        337
Pro Asp Glu Glu Gln Leu Cys Ala Glu Glu Pro Gly Pro Gly Glu Glu
                100                 105                 110 cca gag ccg ggg cag gag ctg gag ccg gaa tcc agg cct gag ctg gaa        385
Pro Glu Pro Gly Gln Glu Leu Glu Pro Glu Ser Arg Pro Glu Leu Glu
             115                 120                 125 tcc atg cct gag ctg gag gca gaa ccg agg cct gag aaa gag tgt gag        433
Ser Met Pro Glu Leu Glu Ala Glu Pro Arg Pro Glu Lys Glu Cys Glu
         130                 135                 140 cag gag ccg gag cag gag ccg gag cag gag ctg gag cag gag ccg gag        481
Gln Glu Pro Glu Gln Glu Pro Glu Gln Glu Leu Glu Gln Glu Pro Glu
     145                 150                 155 ctg gag ccg gag ccg gag ccg gag ccg gag ccg gag ccg gag ccc gag        529
Leu Glu Pro Glu Pro Glu Pro Glu Pro Glu Pro Glu Pro Glu Pro Glu
160                 165                 170                 175 ccc gag ccg gag ccg gag ccc cag cct gcc tat gac cta ctg gat gcc        577
Pro Glu Pro Glu Pro Glu Pro Gln Pro Ala Tyr Asp Leu Leu Asp Ala
                180                 185                 190 aag gag gag cct ggc ctc att gag gcc gag cca gga gat cag caa gcc        625
Lys Glu Glu Pro Gly Leu Ile Glu Ala Glu Pro Gly Asp Gln Gln Ala
             195                 200                 205 gag caa gtg cga gag cag cac gct gaa gct gag gtc atg gct gta gtg        673
Glu Gln Val Arg Glu Gln His Ala Glu Ala Glu Val Met Ala Val Val
         210                 215                 220 gag gag ccg gag agt ctg aag agg agc gcg gag gat gaa cag cct cac        721
Glu Glu Pro Glu Ser Leu Lys Arg Ser Ala Glu Asp Glu Gln Pro His
     225                 230                 235 agt cct ccc aaa cgg ccc agg gag gcg gcg cct ggc gcg ctg gag atg        769
Ser Pro Pro Lys Arg Pro Arg Glu Ala Ala Pro Gly Ala Leu Glu Met
240                 245                 250                 255 gag ccg gct gga gag cgc gag gca gag gcc tgc ccc ttc gtg gag gag        817
Glu Pro Ala Gly Glu Arg Glu Ala Glu Ala Cys Pro Phe Val Glu Glu
                260                 265                 270 cct gac caa gcc cag gaa cag cag act ccg ttg gaa gaa gag gcc aca        865
Pro Asp Gln Ala Gln Glu Gln Gln Thr Pro Leu Glu Glu Glu Ala Thr
             275                 280                 285
```

```
gag gag gca gtc cag ggc ctg atg gtt gga gaa atc gaa ggc ctg          910
Glu Glu Ala Val Gln Gly Leu Met Val Gly Glu Ile Glu Gly Leu
        290                 295                 300 tagtcacggt gtctgtaaaa gagccctctc tacccgttcc tggtgccacc tggctgtggc    970
ttgggaaacc cgctagggcc                                                990

<210> SEQ ID NO 2
<211> LENGTH: 302
<212> TYPE: PRT
<213> ORGANISM: Homo sapiens

<400> SEQUENCE: 2

Met Ser Cys Phe Ser Arg Pro Lys Tyr Lys Thr Gly Asp Leu Val Phe
1               5                   10                  15

Ala Lys Leu Lys Gly Tyr Ala His Trp Pro Ala Arg Ile Glu His Val
            20                  25                  30

Thr Glu Pro Asn Arg Tyr Gln Val Phe Phe Phe Gly Thr His Glu Thr
        35                  40                  45

Ala Leu Leu Gly Pro Lys His Leu Phe Pro Tyr Glu Glu Ser Lys Glu
    50                  55                  60

Arg Phe Gly Lys Pro Asn Lys Arg Arg Gly Phe Ser Glu Gly Leu Trp
65                  70                  75                  80

Glu Ile Glu His Asp Pro Met Ala Glu Ala Ser Pro Cys Leu Cys Pro
                85                  90                  95

Asp Glu Glu Gln Leu Cys Ala Glu Pro Gly Pro Gly Glu Glu Pro
            100                 105                 110

Glu Pro Gly Gln Glu Leu Glu Pro Glu Ser Arg Pro Glu Leu Glu Ser
        115                 120                 125

Met Pro Glu Leu Glu Ala Glu Pro Arg Pro Glu Lys Glu Cys Glu Gln
    130                 135                 140

Glu Pro Glu Gln Glu Pro Glu Gln Glu Leu Glu Gln Glu Pro Glu Leu
145                 150                 155                 160

Glu Pro Glu Pro Glu Pro Glu Pro Glu Pro Glu Pro Glu Pro Glu Pro
                165                 170                 175

Glu Pro Glu Pro Glu Pro Gln Pro Ala Tyr Asp Leu Leu Asp Ala Lys
            180                 185                 190

Glu Glu Pro Gly Leu Ile Glu Ala Glu Pro Gly Asp Gln Gln Ala Glu
        195                 200                 205

Gln Val Arg Glu Gln His Ala Glu Ala Glu Val Met Ala Val Val Glu
    210                 215                 220

Glu Pro Glu Ser Leu Lys Arg Ser Ala Glu Asp Glu Gln Pro His Ser
225                 230                 235                 240

Pro Pro Lys Arg Pro Arg Glu Ala Ala Pro Gly Ala Leu Glu Met Glu
                245                 250                 255

Pro Ala Gly Glu Arg Glu Ala Glu Ala Cys Pro Phe Val Glu Pro
            260                 265                 270

Asp Gln Ala Gln Glu Gln Gln Thr Pro Leu Glu Glu Glu Ala Thr Glu
        275                 280                 285

Glu Ala Val Gln Gly Leu Met Val Gly Glu Ile Glu Gly Leu
    290                 295                 300

<210> SEQ ID NO 3
<211> LENGTH: 21
<212> TYPE: DNA
<213> ORGANISM: Artificial sequence
```

```
<220> FEATURE:
<221> NAME/KEY: misc_feature
<222> LOCATION: (1)..(21)
<223> OTHER INFORMATION: primer

<400> SEQUENCE: 3
cgctatgtct tgcttcagcc g                                              21

<210> SEQ ID NO 4
<211> LENGTH: 21
<212> TYPE: DNA
<213> ORGANISM: Artificial sequence
<220> FEATURE:
<221> NAME/KEY: misc_feature
<222> LOCATION: (1)..(21)
<223> OTHER INFORMATION: primer

<400> SEQUENCE: 4
ggccctagcg ggtttcccaa g                                              21

<210> SEQ ID NO 5
<211> LENGTH: 27
<212> TYPE: DNA
<213> ORGANISM: Artificial sequence
<220> FEATURE:
<221> NAME/KEY: misc_feature
<222> LOCATION: (1)..(27)
<223> OTHER INFORMATION: primer

<400> SEQUENCE: 5
gcaggatcca tgtcttgctt cagccgc                                        27

<210> SEQ ID NO 6
<211> LENGTH: 27
<212> TYPE: DNA
<213> ORGANISM: Artificial sequence
<220> FEATURE:
<221> NAME/KEY: misc_feature
<222> LOCATION: (1)..(27)
<223> OTHER INFORMATION: primer

<400> SEQUENCE: 6
ccgaagcttc aggccttcga tttctcc                                        27

<210> SEQ ID NO 7
<211> LENGTH: 27
<212> TYPE: DNA
<213> ORGANISM: Artificial sequence
<220> FEATURE:
<221> NAME/KEY: misc_feature
<222> LOCATION: (1)..(27)
<223> OTHER INFORMATION: primer

<400> SEQUENCE: 7
gcaaagctta tgtcttgctt cagccgc                                        27

<210> SEQ ID NO 8
<211> LENGTH: 27
<212> TYPE: DNA
<213> ORGANISM: Artificial sequence
<220> FEATURE:
<221> NAME/KEY: misc_feature
<222> LOCATION: (1)..(27)
<223> OTHER INFORMATION: primer

<400> SEQUENCE: 8
ccgggatccc aggccttcga tttctcc                                        27
```

POLYNUCLEOTIDE, VECTOR, HOST CELL AND METHOD FOR PRODUCING HUMAN HEPATOMA-DERIVED GROWTH FACTOR 5 POLYPEPTIDE

FIELD OF INVENTION

This invention relates to the field of genetic engineering, and, in particular, relates to the nucleotide sequence of a human gene. More particularly, this invention relates to the cDNA sequence of human Hepatoma-derived Growth Factor 5 (HDGF5). The invention also relates to the polypeptides encoded by the nucleotide sequence, the uses of these polynucleotides and polypeptides, and the methods for producing them.

BACKGROUND OF TECHNIQUES

Growth factor, known as polypeptide growth factor customarily, is a group of proteins regulating the growth and differentiation of cells and has molecular weight from several hundred to dozens of kilodalton (KD). It is revealed that the regulation of cell growth is mediated by a series of cascade reactions triggered by the interaction between a variety of cytokines and their specific receptors on membrane surfaces. Compared to classical polypeptide and protein hormone, growth factor is released by autocrine and paracrine cells instead of endocrine gland or endocrine cells, so as to achieve the coordination of body and reaction to the environment.

Hepatoma derived growth factor (hepatoma derived growth factor, HDGF) is an important growth factor, which was first reported in paper by Klagsbrun, M et al. in 1986 (P.N.A.S. USA Vol. 33, pp 2448-2452, 1986). In this paper, Klagsbrun, M et al. reported to have isolated and purified a protein factor having 18.5-19 KD from human hepatoma cells line SK-HEP-1. And the remarkable character of this factor was its strong affinity with heparin.

In 1989, a 64 KD factor, also named as HDGF, was first partially purified from HuH-7 cells and characterized by Nakamura et. al. (Clin. Chim. Acta. 183:273-284, 1989). This research group had studied its biochemical characteristics and functions, and found that HDGF was different from PDGF, FGF, HGF. In 1997, this group found the mouse homologue of human HDGF as well as other two members of the gene family, HRP-1 and HRP-2. They all had a highly conserved N-terminal of 98 amino acids. (Biochem. Biophys. Res. Commun. 238: 26-32,1997). In 1999, this research group also cloned HRP-3 (Biochem. Biophys. Res. Commun. 266(1):81-87,1999), another member of HDGF family from human and mouse.

Prior to the publication of this invention, none has disclosed human HDGF5 of the present application.

SUMMARY OF INVENTION

One purpose of the invention is to provide a new polynucleotide which encodes a homologue of HDGF. In the invention, the gene of said homologue of HDGF is named HDGF5.

Another purpose of the invention is to provide a novel protein, which is named HDGF5 protein.

Still another purpose of the invention is to provide a new method for preparing said new HDGF5 protein by recombinant techniques.

The invention also relates to the uses of said HDGF5 protein and its coding sequence.

In one aspect, the invention provides an isolated DNA molecule, which comprises a nucleotide sequence encoding a polypeptide having human HDGF5 protein activity, wherein said nucleotide sequence shares at least 70% homology to the nucleotide sequence of nucleotides 5-910 in SEQ ID NO: 1, or said nucleotide sequence hybridizes to the nucleotide sequence of nucleotides 5-910 in SEQ ID NO: 1 under moderate stringency. Preferably, said nucleotide sequence encodes a polypeptide comprising the amino acid sequence of SEQ ID NO: 2. More preferably, the sequence comprises the nucleotide sequence of nucleotides 5-910 in SEQ ID NO: 1.

Further, the invention provides an isolated HDGF5 polypeptide, which comprises a polypeptide having the amino acid sequence of SEQ ID NO: 2, its active fragments, and its active derivatives.

Preferably, the polypeptide is selected from the group consisting of: (a) a polypeptide having the amino acid sequence of SEQ ID NO: 2. (b) the polypeptide derived from SEQ ID NO: 2 with substitution, deletion, or addition of one or more amino acids and having function of promoting cell proliferation.

The invention also provides a vector comprising said isolated DNA.

The invention further provides a host cell transformed with said vector.

In another aspect, the invention provides a method for producing a polypeptide with the activity of HDGF5 protein, which comprises:

(a) forming a HDGF5 protein expression vector comprising the nucleotide sequence encoding the polypeptide having the activity of HDGF5 protein, wherein said nucleotide sequence is operably linked with an expression regulatory sequences, and said nucleotide sequence shares at least 70% homology to the nucleotide sequence of positions 5-910 in SEQ ID NO: 1;

(b) introducing the vector of step (a) into a host cell, thereby forming a recombinant cell of HDGF5 protein;

(c) culturing the recombinant cell of step (b) under the conditions suitable for the expression of HDGF5 polypeptides;

(d) isolating the polypeptides having the activity of HDGF5 protein.

The invention provides an antibody specifically binding to HDGF5 polypeptide.

The invention further provides a probe, comprising 8-100 consecutive nucleotides shown in SEQ ID NO: 1

DESCRIPTION OF DRAWINGS

FIG. 1 shows the homologue comparison of N-terminal amino acid sequence between HDGF5 and other members of HDGF family. "*" refers to the same amino acid in this site, ":" refers to very high homologue of amino acid, and "." refers to relatively high homologue of amino acid. The GenBank™ accession numbers of these proteins are as follows:

| | |
|---|---|
| Rat HRP | AAL29938 |
| Mouse HRP1 | JC5661 |
| Mouse HDGF | JC5660 |
| Rat HDGF | AAL47132 |
| Human HDGF | D16431 |
| Human HRP1 | AAH18991 |
| Human HRP3 | BAA90477 |

-continued

| | |
|---|---|
| Mouse HRP3 | AB029493 |
| Mouse HRP2 | JC5662 |
| Rat HDGF3 | AAK50635 |

FIG. 1 indicates that the N-terminal of human HDGF5 (HATH region, generally including 98 amino acid residues of N-terminal) and those of other members of HDGF family share high homology.

DETAILED DESCRIPTION OF INVENTION

In the present invention, the term "isolated" or "purified" or "substantially pure" DNA refers to a DNA or fragment which has been isolated from the sequences which frank it in a naturally occurring state. The term also applies to DNA or DNA fragment which has been isolated from other components naturally accompanying the nucleic acid and from proteins naturally accompanying it in the cell.

In the present invention, the term "HDGF5 protein encoding sequence" or "HDGF5 polypeptide encoding sequence" refers to a nucleotide sequence encoding a polypeptide having the activity of HDGF5 protein, such as the nucleotide sequence of positions 5-910 in SEQ ID NO: 1 or its degenerate sequence. The degenerate sequences means the sequences formed by replacing one or more codons in the ORF of 5-910 in SEQ ID NO: 1 with degenerate codes which encode the same amino acid. Because of the degeneracy of codon, the sequence having a homology as low as about 70% to the sequence of nucleotides 5-910 in SEQ ID NO: 1 can also encode the sequence shown in SEQ ID NO: 2. The term also refers to the nucleotide sequences that hybridize to the nucleotide sequence of nucleotides 5-910 in SEQ ID NO: 1 under moderate stringency or preferably under high stringency. In addition, the term also refers to the sequences having a homology of at least 70%, preferably 80%, more preferably 90% to the nucleotide sequence of nucleotides 5-910 in SEQ ID NO: 1.

The term also refers to variants of the sequence in SEQ ID NO: 1, which are capable of encoding a protein having the same function as human HDGF5 protein. These variants includes, but are not limited to, deletions, insertions and/or substitutions of several nucleotides (typically 1-90, preferably 1-60, more preferably 1-20, and most preferably 1-10) and additions of several nucleotides (typically less than 60, preferably 30, more preferably 10, most preferably 5) at 5' end and/or 3' end.

In the present invention, "substantially pure" proteins or polypeptides refers to those which occupy at least 20%, preferably at least 50%, more preferably at least 80%, most preferably at least 90% of the total sample material (by wet weight or dry weight). Purity can be measured by any appropriate method, e.g., in the case of polypeptides by column chromatography, PAGE or HPLC analysis. A substantially purified polypeptides is essentially free of naturally associated components.

In the present invention, the term "HDGF5 polypeptide" or "HDGF5 protein" refers to a polypeptide having the activity of HDGF5 protein comprising the amino acid sequence of SEQ ID NO: 2. The term also comprises the variants of said amino acid sequence which have the same function of human HDGF5. These variants include, but are not limited to, deletions, insertions and/or substitutions of several amino acids (typically 1-50, preferably 1-30, more preferably 1-20, most preferably 1-10), and addition of one or more amino acids (typically less than 20, preferably less than 10, more preferably less than 5) at C-terminal and/or N-terminal. For example, the protein functions are usually unchanged when an amino residue is substituted by a similar or analogous one. Further, the addition of one or several amino acids at C-terminal and/or N-terminal will not change the function of protein. The term also includes the active fragments and derivatives of HDGF5 protein.

The variants of polypeptide include homologous sequences, conservative variants, allelic variants, natural mutants, induced mutants, proteins encoded by DNA which hybridizes to HDGF5 DNA under high or low stringency conditions as well as the polypeptides or proteins retrieved by antisera raised against HDGF5 polypeptide. The present invention also provides other polypeptides, e.g., fusion proteins, which include the HDGF5 polypeptide or fragments thereof. In addition to substantially full-length polypeptide, the soluble fragments of HDGF5 polypeptide are also included. Generally, these fragments comprise at least 10, typically at least 30, preferably at least 50, more preferably at least 80, most preferably at least 100 consecutive amino acids of HDGF5 polypeptide.

The present invention also provides the analogues of HDGF5 protein or polypeptide. Analogues can differ from naturally occurring HDGF5 polypeptide by amino acid sequence differences or by modifications which do not affect the sequence, or by both. These polypeptides include genetic variants, both natural and induced. Induced variants can be made by various techniques, e.g., by random mutagenesis using irradiation or exposure to mutagens, or by site-directed mutagenesis or other known molecular biologic techniques. Also included are analogues which include residues other than those naturally occurring L-amino acids (e.g., D-amino acids) or non-naturally occurring or synthetic amino acids (e.g., beta- or gamma-amino acids). It is understood that the polypeptides of the invention are not limited to the representative polypeptides listed hereinabove.

Modifications (which do not normally alter primary sequence) include in vivo, or in vitro chemical derivation of polypeptides, e.g., acetylation, or carboxylation. Also included are modifications of glycosylation, e.g., those made by modifying the glycosylation patterns of a polypeptide during its synthesis and processing or in the further processing steps, e.g., by exposing the polypeptide to enzymes which affect glycosylation (e.g., mammalian glycosylating or deglycosylating enzymes). Also included are sequences which have phosphorylated amino acid residues, e.g., phosphotyrosine, phosphoserine, phosphothronine, as well as sequences which have been modified to improve their resistance to proteolytic degradation or to optimize solubility properties.

In the present invention, "the conservative variants of peptides of human HDGF5" refers to the polypeptides formed by substitutions of several amino acids (typically 10, preferably 8, more preferably 5, most preferably 3 or less). These conservative variants of polypeptides are preferably produced by substitution of amino acids shown in table 1.

TABLE 1

| Initial residue | Representative substitution | Preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |

TABLE 1-continued

| Initial residue | Representative substitution | Preferred substitution |
|---|---|---|
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The invention also includes antisense sequences of the HDGF5 encoding sequence or its fragments. Said antisense sequence can be used to inhibit expression of HDGF5 in cells.

The invention also includes probes, typically having 8-100, preferably 15-50 consecutive nucleotides of HDGF5 coding sequence. These probes can be used to detect the presence of nucleic acid molecules coding for HDGF5 in samples.

The present invention also includes methods for detecting HDGF5 nucleotide sequences, which comprises hybridizing said probes to samples, and detecting the binding of the probes. Preferably, the samples are products of PCR amplification. The primers in PCR amplification correspond to coding sequence of HDGF5 polypeptide and are located at both ends or in the middle of the coding sequence. In general, the length of the primers is 20 to 50 nucleotides.

In the present invention, various vectors known in the art such as commercially available vectors could be used. For example, a commercially available vector can be operably linked to the nucleic acid sequence encoding the new fusion protein in the present invention under an expression regulatory sequence, and thus forms the expression vector.

As used herein, the term "operably linked" refers to such a condition where a certain part of a linear DNA sequence could affect the activity of another certain part in the same linear DNA sequence. For example, if a signal peptide plays a role in the secretion of polypeptides, then the DNA sequence encoding the signal peptide (precursor sequence of secretion) is operably linked to the DNA of the polypeptide; if a promoter controls the transcription of a sequence, then it is operably linked to the encoding sequence. If a ribosomal binding site is located at a position which can initiate translation, then it is operably linked to the encoding sequence. Generally, "operably linked" means adjacency, while in the precursor sequence of secretion it means adjacency in reading frame.

In the invention, the term "host cells" includes prokaryotic and eukaryotic cells. The common prokaryotic host cells include *Escherichi coli, Bacillus subtilis*, and so on. The common eukaryotic host cells include yeast cells, insect cells, and mammalian cells. Preferably, the host cells are eukaryotic cells, e.g., CHO cells, COS cells, and the like.

In another aspect, the invention also includes antibodies, preferably monoclonal antibodies, which are specific for polypeptides encoded by HDGF5 DNA or fragments thereof. By "specificity", it is meant an antibody which binds to the HDGF5 gene products or a fragments thereof. Preferably, the antibody binds to the HDGF5 gene products or a fragments thereof and does not substantially recognize nor bind to other antigenically unrelated molecules. Antibodies which bind to HDGF5 and block HDGF5 protein and those which do not affect the HDGF5 function are included in the invention. The invention also includes antibodies which bind to the HDGF5 gene product in its unmodified as well as modified form.

The present invention includes not only intact monoclonal or polyclonal antibodies, but also immunologically-active antibody fragments, e.g., a Fab' or (Fab)$_2$ fragment, an antibody light chain, an antibody heavy chain, a genetically engineered single chain Fv molecule, or a chimerical antibody, e.g., an antibody which contains the binding specificity of a murine antibody, but the remaining portion of which is of human origin.

The antibodies in the present invention can be prepared by various techniques known to those skilled in the art. For example, purified HDGF5 gene products, or its antigenic fragments can be administrated to animals to induce the production of polyclonal antibodies. Similarly, cells expressing HDGF5 or its antigenic fragments can be used to immunize animals to produce antibodies. Antibodies of the invention can be monoclonal antibodies which can be prepared by using hybridoma technique (See Kohler, et al., Nature, 256; 495,1975; Kohler, et al., Eur. J. Immunol. 6: 511, 1976; Kohler, et al., Eur. J. Immunol. 6: 292, 1976; Hammerling, et al., In Monoclonal Antibodies and T Cell Hybridomas, Elsevier, N.Y., 1981). Antibodies of the invention comprise those which block HDGF5 function and those which do not affect HDGF5 function. Antibodies in the invention can be produced by routine immunology techniques and using fragments or functional regions of HDGF5 gene product. These fragments and functional regions can be prepared by recombinant methods or synthesized by a polypeptide synthesizer. Antibodies binding to unmodified HDGF5 gene product can be produced by immunizing animals with gene products produced by prokaryotic cells (e.g., *E. coli*); antibodies binding to post-translationally modified forms thereof can be acquired by immunizing animals with gene products produced by eukaryotic cells (e.g., yeast or insect cells).

The full length human HDGF5 nucleotide sequence or its fragment of the invention can be prepared by PCR amplification, recombinant method and synthetic method. For PCR amplification, one can obtain said sequences by designing primers based on the nucleotide sequence disclosed in the invention, especially the sequence of ORF, and using cDNA library commercially available or prepared by routine techniques known in the art as a template. When the sequence is long, it is usually necessary to perform two or more PCR amplifications and link the amplified fragments together in the correct order.

Once the sequence is obtained, a great amount of the sequences can be produced by recombinant methods. Usually, said sequence is cloned in a vector which is then transformed into a host cell. Then the sequence is isolated from the amplified host cells using conventional techniques.

Further, the sequence can be produced by synthesis. Typically, several small fragments are synthesized and linked together to obtain a long sequence. At present, it is completely feasible to chemically synthesize the DNA sequence encoding the protein of the invention, or the fragments or derivatives thereof. In addition, the mutation can be introduced into the sequence of the protein by chemical synthesis.

In addition to recombinant techniques, the protein fragments of the invention may also be prepared by direct chemical synthesis using solid phase synthesis techniques (Stewart et al., (1969) Solid-Phase Peptide Synthesis, WH Freeman Co., San Francisco; Merrifield J. (1963), J. Am. Chem. Assoc. 85: 2149-2154). In vitro protein synthesis can be performed manually or automatically, e.g., using a Model 431A Peptide Synthesizer (Applied Biosystems, Foster City, Calif.). The fragments of protein of the invention can be synthesized separately and linked together using chemical methods so as to produce full-length molecule.

The sequences encoding the protein of the present invention are also valuable for gene mapping. For example, the accurate chromosome mapping can be performed by hybridizing cDNA clones to a chromosome in metaphase. This FISH technique can use cDNA as short as about 500 bp, or as long as about 2000 bp, or more. For details, see Verma et al., Human Chromosomes: A Manual of Basic Techniques, Pergamon Press, New York (1988).

Once a sequence has been mapped to a precise chromosomal location, the physical position of the sequence on the chromosome can be correlated with genetic map data. Such data are found in, e.g., Mendelian Inheritance in Man (available on-line through Johns Hopkins University Welch Medical Library). The relationships between genes and diseases that have been mapped to the same chromosomal region are then identified through linkage analysis.

Then, the differences in the cDNA or genomic sequence between affected and unaffected individuals can also be determined. If a mutation is observed in some or all of the affected individuals but not in any normal individual, then the mutation is likely to be the causative agent of the disease.

The substances which act with the HDGF5, e.g., receptors, inhibitors and antagonists, can be screened out by various conventional techniques, using the protein of the invention.

The protein, antibody, inhibitor, antagonist or receptor of the invention provide different effects when administered in therapy. Usually, these substances are formulated with a non-toxic, inert and pharmaceutically acceptable aqueous carrier. The pH typically ranges from 5 to 8, preferably from about 6 to 8, although pH may alter according to the property of the formulated substances and the diseases to be treated. The formulated pharmaceutical composition is administrated in conventional routine including, but not limited to, intramuscular, intraperitoneal, subcutaneous, intracutaneous, or topical administration.

As an example, the human HDGF5 protein of the invention may be administrated together with the suitable and pharmaceutically acceptable carrier. The examples of carriers include, but are not limited to, saline, buffer solution, glucose, water, glycerin, ethanol, or the combination thereof. The pharmaceutical formulation should be suitable for the delivery method. The human HDGF5 protein of the invention may be in the form of injections which are made by conventional methods, using physiological saline or other aqueous solution containing glucose or auxiliary substances. The pharmaceutical compositions in the form of tablet or capsule may be prepared by routine methods. The pharmaceutical compositions, e.g., injections, solutions, tablets, and capsules, should be manufactured under sterile conditions. The active ingredient is administrated in therapeutically effective amount, e.g., from about 1 ug to 10 mg per kg body weight per day. Moreover, the polypeptide of the invention can be administrated together with other therapeutic agent.

When the human HDGF5 polypeptides of the invention are used as a pharmaceutical, the therapeutically effective amount of the polypeptides are administrated to mammals. Typically, the therapeutically effective amount is at least about 1 ug/kg body weight and less than about 10 mg/kg body weight in most cases, and preferably about 10 ug-1 mg/kg body weight. Of course, the precise amount will depend upon various factors, such as delivery methods, the subject health, and the like, and is within the judgment of the skilled clinician.

In one embodiment, the cDNA sequence of HDGF5 was obtained as follows: human testis λgt11 cDNA library (Clontech™) was used as a template and PCR was carried out with the synthetic forward primer A1: 5'-CGCTAT-GTCTTGCTTCAGCCG-3'(SEQ ID NO: 3) and reverse primer A2:5'-GGCCCTAGCGGGTTTCCCAAG-3'(SEQ ID NO:4). The PCR condition are 4 min at 93° C., followed by 35 cycles with 1 min at 93° C., 1 min at 68° C., 1 min at 72° C., and finally 5 min at 72° C. The target fragments of about 1000 bp were obtained. The detailed sequence of 990 bp nucleotides was shown in SEQ ID NO: 1 and the ORF comprises the nucleotides 5-910.

Hepatoma-derived Growth Factor (HDGF) is a hepatin-binding protein isolated from human hepatoma-derived cell line HuH-7. HDGF has the activity of stimulating cell growth and promoting the growth of fibroblast and some heptoma cells. The mitogenic activity of HDGF implied the great application value of HDGF in treating pernicious oxyhepatitis and liver injury.

It is indicated in the researches that although HDGF is derived from the hepatoma cell lines, it is widely expressed both in normal cells and tumor cell lines. Therefore, HDGF not only affects the tumor cells, and also plays important roles in the physiological and developmental process of normal tissues and cells. For example, HDGF stimulates cell division of SMC, COS-7, Swiss-3T3, HuH-7, 7.1.1, promotes and regulates the growth of blood vessel endothelium cells and leiomyocytes, and plays physiological roles as secretory growth factor or nucleus factor. The expression patterns of the HDGF gene family members are different. However, they are all enriched in testis and the 5'-untranslated region contains GC-rich nucleotide sequences (GC content>70%), suggesting their potential important roles in male germ-cell development. They may also relate to DNA methylation, chromatin conformation, and translational regulation.

HDGF5 in the present invention can promote the proliferation of liver cell after partial liver tissue had been cut. The small molecule antagonists or inhibitors against HDGF5 can be found and produced as medicines to suppress the growth of hepatoma cells and induce apoptosis, and therefore, slow or control the symptom of hepatocellular carcinoma. Because HDGF5 has different expression pattern in various cells, the HDGF5 protein, its coding nucleotide sequence or its active part can be developed into special kits to diagnose the early stage of carcinoid and malignant tumor and evaluate the treatment effect and prognosis after HCC surgery.

HDGF5 stimulates mitosis of various cells in varying degrees. It can also be used in regulating the growth of blood vessel endothelium cells and leiomyocytes so that HDGF5 has certain application value in promoting wound healing, treating injury of acute inflammation, malignant tumor other than liver cancer.

In addition, human HDGF5 of the invention has human derived natural amino acid sequence. So compared with HDGF proteins derived from other species, it will have higher activity or less by-effect (e.g. lesser or no immunogenicity in human body) in treating human disease.

The invention is further illustrated by the following examples. It is appreciated that these examples are only intended to illustrate the invention, but not to limit the scope of the invention. For the experimental methods in the following examples, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

EXAMPLE 1

The Cloning and Sequencing of HDGF5 cDNA Sequence

1. Amplification With Primers

The template was human testis λgt 11 cDNA library (commercially available from CLONTECH™). PCR was carried out with the forward primer A1: 5'-CGCTATGTCT-TGCTTCAGCCG-3' (SEQ ID NO: 3) and reverse primer A2: 5'-GGCCCTAGCGGGTTTCCCAAG-3' (SEQ ID NO: 4). The PCR condition was 4 mins at 93° C.; followed by 35 cycles with 1 min at 93° C., 1 min at 68° C., and 1 min at 72° C.; and, finally 5 mins at 72° C. The PCR fragments were detected by electrophoresis. The target fragment was about 1000 bp.

2. Sequencing PCR Products

The above obtained PCR products were linked with pGEM-T™ vector (Promega) and transformed into *E. coli* JM103. The plasmids were extracted using QIAprep Plasmid Kit (QIAGEN™). The oriented serial deletion of the inserted fragments was carried out with Double-Stranded Nested Deletion Kit (Pharmacia), and the deletants were quickly identified by PCR and arranged in order. The deletants successively cut-off were sequenced with SequiTherm EXCEL™ DNA Sequencing Kit (Epicentre Technologies). A full length cDNA sequence of 990 bp was obtained by overlapping the sequences with computer software. The detailed sequence is shown in SEQ ID NO: 1.

```
cgctatgtct tgcttcagcc gcccaaaata caagaccggg gacctggtgt ttgccaaatt   60 (SEQ ID NO: 1)

aaagggctat gcccattggc cagcgaggat tgaacatgtc actgaaccca accgctacca  120
ggtgttcttc ttcgggaccc atgagaccgc cctgctgggc cccaagcacc tttttcctta  180
tgaggagtcc aaggagaggt tcggcaagcc taacaagagg cgcggcttca gtgaggggct  240
gtgggagatc gagcacgacc ctatggctga ggcctcccct tgcctgtgcc cagatgagga  300
gcagctttgt gccgaggagc cagggccagg agaggagcca gagccggggc aggagctgga  360
gccggaatcc aggcctgagc tggaatccat gcctgagctg gaggcagaac cgaggcctga  420
gaaagagtgt gagcaggagc cggagcagga gccggagcag gagctggagc aggagccgga  480
gctggagccg gagccggagc cggagccgga gccggagccg gagcccgagc ccgagccgga  540
gccggagccc cagcctgcct atgacctact ggatgccaag gaggagcctg gcctcattga  600
ggccgagcca ggagatcagc aagccgagca agtgcgagag cagcacgctg aagctgaggt  660
catggctgta gtggaggagc cggagagtct gaagaggagc gcggaggatg aacagcctca  720
cagtcctccc aaacggccca gggaggcggc gcctggcgcg ctggagatgg agccggctgg  780 agagegagag gcagaggcct gccccttcgt ggaggagcct gaccaagccc aggaacagca  840
gactccgttg gaagaagagg ccacagagga ggcagtccag ggcctgatgg ttggagaaat  900
cgaaggcctg tagtcacggt gtctgtaaaa gagccctctc tacccgttcc tggtgccacc  960
tggctgtggc ttgggaaacc cgctagggcc.                                  990
```

50

According to the resultant full-length cDNA sequence, the amino acid sequence of HDGF5 was deduced, having 302 amino acid residues totally. See SEQ ID NO:2 for its amino acid sequence in details.

```
MSCFSRPKYK TGDLVFAKLK GYAHWPARIE HVTEPNRYQV FFFGTHETAL LGPKHLFPYE   60 (SEQ ID NO: 2)

ESKERFGKPN KRRGFSEGLW ELEHDPMAEA SPCLCPDEEQ LCAEEPGPGE EPEPGQELEP  120

ESRPELESMP ELEAEPRPEK ECEQEPEQEP EQELEQEPEL EPEPEPEPEP EPEPEPEPEP  180

EPQPAYDLLD AKEEPGLIEA EPGDQQAEQV REQHAEAEVM AVVEEPESLK RSAEDEQPHS  240

PPKRPREAAP GALEMEPAGE REAEACPFVE EPDQAQEQQT PLEEEATEEA VQGLMVGEIE  300

GL 302
```

EXAMPLE 2

Homologous Comparison

The full length cDNA sequence of human HDGF5 and the encoded protein were used for homologous searching Non-redundant GenBank+EMBL+DDBJ+PDB and on-redundant GenBank CDS translations+PDB+SwissProt+Spupdate+PIR databases by BLAST algorithm. The N-terminal of the HDGF family has high conservative region (HATH region, for homologous to the amino terminus of the HDGF). This region is regarded as the signature sequence. The N-terminal of human HDGF5 shared high homologous with those of other HDGF family members (See the homologous comparison of N-terminal sequence between HDGF5 and other members of HDGF family in FIG. 1). Therefore, it was indicated that HDGF5 was a member of HDGF family and had functions similar to those of other members.

Hepatoma-derived Growth Factor (HDGF) is a hepatin-binding protein isolated from human hepatoma-derived cell line HuH-7. HDGF has the activity of stimulating cell growth and promoting the growth of fibroblast and some heptoma cells (J. Biol. Chem. 269(40): 25143-25149, 1994). The mitogenic activity of HDGF implied the great application value of HDGF in treating pernicious oxyhepatitis and liver injury.

It is indicated in the researches that although HDGF is derived from the hepatoma cell lines, it is widely expressed both in normal cells and tumor cell lines. Therefore, HDGF not only affects the tumor cells, and also plays important roles in the physiological and developmental process of normal tissues and cells. For example, HDGF stimulates cell division of SMC, COS-7, Swiss-3T3, HuH-7, 7.1.1, promotes and regulates the growth of blood vessel endothelium cells and leiomyocytes, and plays physiological roles as secretory growth factor or nucleus factor.

The HDGF5 of the invention can be used to produce fusion proteins with other proteins, such as immunoglobulins. Besides, HDGF5 can be fused with or exchange fragments with other members of the family to form new proteins. For example, the N terminal of HDGF5 can exchange with the N terminal of other HDGFs or mice HDGF to produce proteins, which are more active or have new properties.

The antibodies against HDGF5 can be used to screen other members of the family or to purify the related proteins such as other members of the family through affinity purification.

Moreover, HDGF5 nucleic acid (coding sequence and antisense sequence) could be induced into cell to enhance the expression level of HDGF5 or inhibit the over-expression of HDGF5. Human HDGF5 protein or its active polypeptide fragment could be used to treat patients whose HDGF5 was lacking, no function or abnormal. In addition, the nucleic acid sequence or antibody of the invention could be used in diagnosis or prognosis judgment.

EXAMPLE 3

Expression of HDGF5 in E. coli

In this example, the cDNA sequence encoding HDGF5 was amplified with oligonucleotide PCR primers corresponding to 5'- and 3'-end of said DNA sequence.

The sequence of 5'-end oligonucleotide primer was:

```
                                          (SEQ ID NO: 5)
E1: 5'-GCAGGATCCATGTCTTGCTTCAGCCGC-3'.
```

This primer contained a cleavage site of restriction endonuclease BamHI, followed by partial nucleotides of HDGF5 coding sequence starting from the start codon.

The sequence of 3'-end primer was:

```
                                          (SEQ ID NO: 6)
E2: 5'-CCGAAGCTTCAGGCCTTCGATTTCTCC-3'.
```

This primer contained a cleavage site of restriction endonuclease HindIII, a translation terminator and partial HDGF5 coding sequence.

These cleavage sites of restriction endonuclease in primers corresponded to the cleavage sites in bacterial expression vector pQE-9 (Qiagen Inc., Chatsworth, Calif.). Vector pQE-9 encodes an antibiotic resistance ($Amp^r$), a bacterial replication origin (ori), an IPTG-adjustable promotor/operon (P/O), a ribosome-binding site (RBS), a six-hisitine tag (6-His) and cloning sites of restriction endonuclease.

Vector pQE-9 and insertion fragments were digested by BamHI and HindIII, and then linked together. Then, the linkage mixture was used to transform E. coli M15/rep4 (QIAGEN) containing multi-copy of plasmid pREP4 which expressed repressor of lacI and was resistant to kanamycin ($Kan^r$). Transformants were screened out in LB medium containing Amp and Kan. The plasmids were extracted. The size and direction of the inserted fragments were verified by EcoNI digestion. The sequencing confirmed that HDGF5 cDNA fragment was correctly inserted into the vector.

The positive clones of transformant were cultured overnight in LB liquid medium supplemented with Amp (100 ug/ml) and Kan (25 ug/ml). The overnight culture was 1:100-1:250 diluted, inoculated into large volume medium, and cultured until the 600 nm optical density ($OD_{600}$) reached 0.4-0.6. IPTG (isopropylthio-beta-D-galactoside) was added to final concentration of 1 mM. By deactivating repressor of LacI, IPTG induced and promoted P/O, thereby increasing the expression of gene. The cells were cultured for another 3-4 hours, and then centrifuged (6000×g, 20 mins). The cultures were sonicated, and cell lysate was collected and diluted with 6M guanidine hydrochloride. After clarification, the dissolved HDGF5 in solution were purified by nickel-chelated column chromatography under the conditions suitable for the tight binding of 6-His tagged protein and column. HDGF5 was eluted with 6M guanidine hydrochloride (pH 5.0). The denaturalized proteins in guanidine hydrochloride were precipitated by several methods. First, guanidine hydrochloride was separated by dialysis. Alternatively, the purified protein, which was isolated from nickel-chelated column, bound to the second column with decreased linear gradient of guanidine hydrochloride. The proteins were denatured when binding to the column. Then, the proteins were eluted with guanidine hydrochloride (pH 5.0). Finally, the soluble proteins were dialyzed with PBS, then preserved in glycerol stock solution with the final glycerol concentration of 10% (w/v).

The molecular weight of the expressed protein was about 34148 Da, as identified by 12% SDS-PAGE.

Moreover, the sequencing results of the 10 amino acids at the N- and C-terminal of the expressed protein indicated that they were identical to those in SEQ ID NO: 2.

EXAMPLE 4

Expression of HDGF5 in Eukaryotic Cells (CHO Cell Line)

In this example, the cDNA sequence encoding HDGF5 was amplified with oligonucleotide PCR primers corresponding to 5'- and 3'-end of DNA sequence. The resultant product was used as an insertion fragment.

The sequence of 5'-end oligonucleotide primer was:

(SEQ ID NO: 7)
C1: 5'-GCAAAGCTTATGTCTTGCTTCAGCCGC-3'

This primer contained a cleavage site of restriction endonuclease HindIII, followed by 18 nucleotides of HDGF5 coding sequence starting from the start codon.
The sequence of 3'-end primer was:

(SEQ ID NO: 8)
C2: 5'-CCGGGATCCCAGGCCTTCGATTTCTCC-3'

This primer contained a cleavage site of restriction endonuclease BamHI, a translation stop codon, and partial HDGF5 coding sequence.

These cleavage sites of restriction endonuclease in primers corresponded to the cleavage sites in expression vector pcDNA3 for CHO cell. This vector encoded two kinds of antibiotic resistance ($Amp^r$ and $Neo^r$), a phage replication origin (fl ori), a virus replication origin (SV40 ori), a T7 promoter, a virus promoter (P-CMV), a Sp6 promoter, a polyadenylation signal of SV40 and the corresponding polyA sequence thereof, a polyadenylation signal of BGH and the corresponding polyA sequence thereof.

The vector pcDNA3 and insertion fragment were digested with HindIII and BamHI, and linked together. Subsequently, E. coli strand DH5α was transformed with linkage mixture. Transformants were screened out in LB medium containing Amp. The clones containing the needed constructs were cultured overnight in LB liquid medium supplemented with Amp (100 ug/ml). Plasmids were extracted. The size and direction of the inserted fragments were verified by EcoNI digestion. The sequencing indicated that HDGF5 cDNA fragment was correctly inserted into the vector.

Plasmids were transfected into CHO cells by lipofection with Lipofectin™ Kit (GIBco Life). After transfecting the cells for 48 hours and screening the cells with G418 for 2-3 weeks, the cells and cell supernatant were collected and the activity of the expressed protein was measured. G418 was removed and the transformants were subcultured continuously. The mixed clonal cells were limiting diluted and the subclones with higher protein activity were selected. The positive subclones were mass cultured by routine methods. 48 hours later, the cells and supernatant were collected. The cells were ultrasonicated. Using 50 mM Tris-HCl (pH7.6) solution containing 0.05% Triton as an equilibrium solution and eluent, the active peek of the protein was collected with a pre-balanced Superdex G-75 column. Then, using 50 mM Tris-HCl (pH8.0) solution containing 0-1 M NaCl as an eluent, the protein was gradiently washed on a DEAE-Sepharose column balanced with 50 mM Tris-HCl (pH8.0) solution. The active peek of the protein was collected. The solution of the expressed protein was dialyzed with PBS (pH7.4), and finally lyophilized and preserved.

The molecular weight of the expressed protein was 34 KDa as identified by 12% SDS-PAGE.

Moreover, the sequencing results of the 10 amino acids at the N- and C-terminal of the expressed protein indicated that they were identical to those in SEQ ID NO: 2.

EXAMPLE 5

Antibody Preparation

Antibodies were produced by immunizing animals with the recombinant proteins obtained in Examples 3 and 4. The method was as follows: the recombinant proteins were isolated by chromatography, and stored for use. Alternatively, the protein was isolated by SDS-PAGE electrophoresis, and obtained by cutting electrophoretic bands from gel. The protein was emulsified with Freund's complete adjuvant of the same volume. The emulsified protein was injected intraperitoneally into mice at a dosage of 50-100 ug/0.2 ml. 14 days later, the same antigen was emulsified with Freund's incomplete adjuvant and injected intraperitoneally into mice at a dosage of 50-100 ug/0.2 ml for booster immunization. Booster immunization was carried out every 14 days, for at least three times. The specific activity of the obtained antiserum was evaluated by its ability of precipitating the translation product of HDGF5 gene in vitro. The result showed that the antibody specifically bound to HDGF5 protein of the invention.

EXAMPLE 6

Promotion Effect of HDGF5 on Cell Proliferation

The promotion effect of HDGF5 on cell proliferation effect was tested by adding various concentrations of HDGF5. The detailed protocols were as follows: The mouse endothelium cell Berd-3 was planted into 96-hole panel with 10% 1640 medium to final concentration of $1-1.2 \times 10^4$ cells/ml. The cells were incubated in the incubator (5% $CO_2$) at 37° C. overnight. The primary medium was substituted with serum-free medium and the cells were incubated in the incubator (5% $CO_2$) at 37° C. overnight again. The purified HDGF5 protein prepared in Example 4 was added into the holes containing the mouse endothelium cells. The concentrations of HDGF5 were gradiently diluted in each holes, i.e., 0 (blank control), 0.1 ng/ml, 0.5 ng/ml, 2.5 ng/ml, 25 ng/ml, 100 ng/ml. After adding various concentrations of HDGF5, these cells were cultured again at 37° C. and 5% $CO_2$, and stopped at 24, 48, 72 hours respectively to test MTS.

The test results indicated that as the content of HDGF5 increased, the cell number was increased correspondingly.

All the documents cited herein are incorporated into the invention as reference, as if each of them is individually incorporated. Further, it is appreciated that, in the above teaching of the invention, the skilled in the art can make certain changes or modifications to the invention, and these equivalents are still within the scope of the invention defined by the appended claims of the present application.

The invention claimed is:

1. An isolated DNA molecule comprising a nucleotide sequence encoding a human hepatoma-derived growth factor 5 (HDGF5) polypeptide having an activity of proliferation of mouse endothelium cells, wherein said nucleotide sequence encodes a polypeptide comprising the amino acid sequence of SEQ ID NO: 2.

2. The DNA molecule of claim 1 wherein said nucleotide sequence encodes a polypeptide consisting of the amino acid sequence of SEQ ID NO: 2.

3. The DNA molecule of claim 1 wherein said nucleotide sequence comprises nucleotides 5-910 in SEQ ID NO: 1.

4. A vector containing the DNA molecule of claim 1.

5. A host cell transformed by the vector of claim 4.

6. A method for producing a human hepatoma-derived growth factor 5 (HDGF5) polypeptide having the activity of proliferation of mouse endothelium cells, which comprises the steps of:

(a) forming an expression vector comprising a nucleotide sequence encoding the HDGF5 polypeptide having the activity of proliferation of mouse endothelium cells, wherein said nucleotide sequence is operably linked with an expression regulatory sequences, and said nucleotide sequence encodes a polypeptide comprising the amino acid sequence of SEQ ID NO: 2;

(b) introducing the vector of step (a) into a host cell, thereby forming a recombinant cell;

(c) culturing the recombinant cell of step (b) under the conditions suitable for expression of HDGF5 polypeptide; and (d) isolating the HDGF5 polypeptides so produced.

7. The method of claim 6 wherein said nucleotide sequence comprises nucleotides 5-910 in SEQ ID NO: 1.

* * * * *